(12) United States Patent
Huang

(10) Patent No.: US 10,772,446 B2
(45) Date of Patent: Sep. 15, 2020

(54) AIR-BAG-LIFTING SLEEP PILLOW STRUCTURE

(71) Applicant: Hsien-Ta Huang, Taoyuan (TW)

(72) Inventor: Hsien-Ta Huang, Taoyuan (TW)

(\*) Notice: Subject to any disclaimer, the term of this patent is extended or adjusted under 35 U.S.C. 154(b) by 481 days.

(21) Appl. No.: 15/672,620

(22) Filed: Aug. 9, 2017

(65) Prior Publication Data
US 2018/0042408 A1     Feb. 15, 2018

(30) Foreign Application Priority Data

Aug. 15, 2016   (TW) .............................. 105212339 A
Dec. 23, 2016   (TW) .............................. 105219582 A

(51) Int. Cl.
*A47G 9/10*     (2006.01)
*A61B 5/11*     (2006.01)
*A61B 5/00*     (2006.01)

(52) U.S. Cl.
CPC ......... *A47G 9/1027* (2013.01); *A47G 9/1009* (2013.01); *A61B 5/1116* (2013.01); *A61B 5/68* (2013.01); *A61B 5/6892* (2013.01)

(58) Field of Classification Search
CPC .. A47G 9/1027; A47G 9/1009; A61B 5/1116; A61B 5/68; A61B 5/6892; B25H 1/0035; A47B 2200/0052; A47B 2220/0025; A61G 7/072; A47C 20/048
USPC ................................... 5/636; 92/44; 267/122
See application file for complete search history.

(56) References Cited

U.S. PATENT DOCUMENTS

| | | | | |
|---|---|---|---|---|
| 1,351,843 A * | 9/1920 | Dunn | ..................... | B60G 13/08 267/64.25 |
| 1,745,959 A * | 2/1930 | Steiner | ..................... | B66F 3/35 92/44 |
| 1,928,368 A * | 9/1933 | Coffey | ..................... | B60S 9/12 92/43 |
| 2,350,711 A * | 6/1944 | Amos | ................... | A47C 23/047 267/117 |
| 2,668,964 A * | 2/1954 | Simmons | ................. | B62H 5/00 5/657 |
| 2,817,096 A * | 12/1957 | Roth | .................... | A61G 7/1059 4/579 |
| 3,251,077 A * | 5/1966 | Beckman | ............... | A47C 31/02 267/117 |
| 3,255,470 A * | 6/1966 | Knittel | .................. | A47C 23/047 267/117 |
| 3,261,037 A * | 7/1966 | Cermak | ................... | A47C 4/54 267/117 |
| 3,263,247 A * | 8/1966 | Knittel | ................... | A47C 27/06 267/117 |
| 3,280,410 A * | 10/1966 | Propst | ...................... | A47C 4/54 267/119 |

(Continued)

*Primary Examiner* — Nicholas F Polito
*Assistant Examiner* — Luke Hall
(74) *Attorney, Agent, or Firm* — Chun-Ming Shih

(57) ABSTRACT

A sleep pillow structure includes a posture-sensing and commanding device, a signal-receiving and inflating-deflating control unit, and a height control unit. The height control unit includes an air pump, a vent valve, pipes, and a lifting device. The posture-sensing and commanding device is installed on a human body to detect the human body's sleep posture, and to send a signal about the human body's sleep posture to the sleep pillow in a wired or wireless manner, such that the height control unit automatically adjusts the height of the sleep pillow to adapt to a user's sleep posture.

7 Claims, 12 Drawing Sheets

(56) References Cited

U.S. PATENT DOCUMENTS

| | | | | | |
|---|---|---|---|---|---|
| 3,682,431 | A | * | 8/1972 | Vivian | A47C 7/14 248/631 |
| 3,784,994 | A | * | 1/1974 | Kery | A47C 23/002 5/710 |
| 3,879,776 | A | * | 4/1975 | Solen | A47C 27/081 5/665 |
| 4,005,858 | A | * | 2/1977 | Lochner | F16F 9/30 267/136 |
| 4,046,348 | A | * | 9/1977 | Goodwin | A47C 3/40 248/423 |
| 4,099,276 | A | * | 7/1978 | Hunt | A61G 7/002 5/615 |
| 4,437,702 | A | * | 3/1984 | Agosta | A47C 31/126 297/284.8 |
| 4,501,034 | A | * | 2/1985 | Greenawalt | A47G 9/10 5/636 |
| 4,528,705 | A | * | 7/1985 | Greenawalt | A47G 9/10 5/636 |
| 4,538,854 | A | * | 9/1985 | Wilson | A47C 3/30 297/344.2 |
| 4,542,547 | A | * | 9/1985 | Sato | A47C 27/082 5/713 |
| 4,605,203 | A | * | 8/1986 | Hooper | F15B 15/10 254/93 H |
| 4,629,253 | A | * | 12/1986 | Williams | B60N 2/00 297/284.1 |
| 4,674,911 | A | * | 6/1987 | Gertz | F16F 9/049 256/13.1 |
| 4,694,515 | A | * | 9/1987 | Rogers, Jr. | A47C 17/22 137/223 |
| 4,778,216 | A | * | 10/1988 | Stupakis | A47C 3/40 248/157 |
| 4,782,542 | A | * | 11/1988 | Sato | A47C 20/048 5/424 |
| 4,825,681 | A | * | 5/1989 | Smedberg | B21D 24/02 100/259 |
| 4,827,546 | A | * | 5/1989 | Cvetkovic | A47C 27/061 297/DIG. 8 |
| 4,852,195 | A | * | 8/1989 | Schulman | A61G 7/05776 5/713 |
| 4,856,626 | A | * | 8/1989 | Nakanishi | F16F 3/08 188/371 |
| 5,029,939 | A | * | 7/1991 | Smith | A61G 7/05776 297/284.1 |
| 5,060,328 | A | * | 10/1991 | Larson | A47C 27/085 297/DIG. 8 |
| 5,492,300 | A | * | 2/1996 | Riihiluoma | B66F 3/22 248/354.1 |
| 6,004,116 | A | * | 12/1999 | Wang | A47C 27/081 417/472 |
| 6,023,801 | A | * | 2/2000 | Lamm | A47G 9/1009 5/636 |
| 6,126,152 | A | * | 10/2000 | Santos | F16F 9/04 267/118 |
| 6,189,167 | B1 | * | 2/2001 | Tsai | A61G 7/0573 5/636 |
| 6,739,009 | B2 | * | 5/2004 | del Drago | A47C 27/082 5/655.3 |
| 6,851,146 | B1 | * | 2/2005 | Kristof | A45D 44/10 5/636 |
| 6,951,038 | B1 | * | 10/2005 | Ganoe, Sr. | A47G 9/1027 5/636 |
| 6,996,865 | B2 | * | 2/2006 | Sabin | A47C 23/00 267/91 |
| 7,546,653 | B2 | * | 6/2009 | Ye | A47C 21/044 5/421 |
| 7,774,881 | B2 | * | 8/2010 | Friedrichs | A47C 27/082 5/710 |
| 7,926,787 | B2 | * | 4/2011 | Wieland | A63G 31/12 254/93 HP |
| 7,971,296 | B2 | * | 7/2011 | Jansen | A47C 21/006 5/109 |
| 8,007,417 | B2 | * | 8/2011 | Heller | A63B 22/18 482/112 |
| 8,074,559 | B2 | * | 12/2011 | Altobelli | A61F 5/012 92/43 |
| 8,122,545 | B2 | * | 2/2012 | Wilkinson | A47C 27/084 5/654 |
| 8,341,784 | B2 | * | 1/2013 | Scott | A47G 9/1027 5/636 |
| 8,418,294 | B1 | * | 4/2013 | Davis | A47G 9/1009 5/630 |
| 8,733,844 | B1 | * | 5/2014 | Widmer | B64D 11/0619 297/452.41 |
| 8,863,336 | B2 | * | 10/2014 | Theosabrata | A47C 19/025 5/652.1 |
| 9,015,884 | B2 | * | 4/2015 | Herrnsdorf | A47G 9/10 5/636 |
| 9,675,508 | B2 | * | 6/2017 | Hall | B66F 3/247 |
| 9,975,747 | B1 | * | 5/2018 | Williams | B66F 3/35 |
| 2002/0050112 | A1 | * | 5/2002 | Koch | F16C 33/3856 52/651.07 |
| 2004/0097837 | A1 | * | 5/2004 | Brandon | A63B 23/0244 600/587 |
| 2004/0128769 | A1 | * | 7/2004 | Azoulay | A47G 9/1009 5/640 |
| 2006/0040803 | A1 | * | 2/2006 | Perez, Jr. | A63B 21/05 482/112 |
| 2007/0118991 | A1 | * | 5/2007 | Nakayama | A47G 9/1009 5/640 |
| 2008/0168605 | A1 | * | 7/2008 | Wolske | A61F 7/08 5/644 |
| 2008/0256710 | A1 | * | 10/2008 | Ho | A61F 5/56 5/636 |
| 2009/0094750 | A1 | * | 4/2009 | Oguma | A61F 5/56 5/636 |
| 2009/0276960 | A1 | * | 11/2009 | Chou | A47G 9/1009 5/640 |
| 2014/0142485 | A1 | * | 5/2014 | Berry | A61B 5/1116 602/19 |
| 2016/0058429 | A1 | * | 3/2016 | Shinar | A61B 10/0012 600/551 |
| 2016/0310062 | A1 | * | 10/2016 | Larson | A61B 5/742 |
| 2017/0027498 | A1 | * | 2/2017 | Larson | A61G 7/057 |

* cited by examiner

AIR-BAG-LIFTING SLEEP PILLOW STRUCTURE

BACKGROUND OF THE INVENTION

1. Technical Field

The present invention relates to sleep pillows, and more particularly to an air-bag-lifting sleep pillow structure, which can automatically adapt its height to a user's real-time sleep posture.

2. Description of Related Art

Sleep takes up more than one third time of our whole life. Sufficient sleep is essential to good health. Only when having quality sleep, a man can really relieve fatigue after a busy day and get refreshed for facing another busy day.

However, in modern times, many people living under pressure have trouble sleeping despite their physical exhaustion. Even if they can sleep, any small movement can wake them up because they never really reach deep sleep. Without sufficient and quality sleep, one can mess up his sleep schedule and fall into a vicious cycle where his poor sleep quality leads to an endocrine disorder that disturbs sleep even more. According to medical research, people with long-term insomnia live fifteen years fewer than people sleeping well on average, and they are more likely to suffer from skin aging, diabetes, hypertension, melancholia and cardiopathy. In some cases, insomnia can cause a decrease in immunity by 50%.

When we investigate in why sleeplessness happen, one major cause is related to unfit sleep pillows. Since body figures vary from person to person, the required height of sleep pillows is different. A burly person may need his pillow relatively high, and a slim person may need his pillow relatively low. Another consideration is that people change sleep posture naturally over time as a biological response to prevent local overpressure and muscle soreness. For example, a person can repeatedly change his posture between sleeping on his back and on his side in one night. When sleeping on his back and on his side, a person has his head positioned differently, meaning that the clearance between his neck and the bed surface varies as he changes sleep postures. Particularly, when a person sleeps on his back, his neck is relatively close to the bed surface, and at this time, his sleep pillow is preferably low in height. When he sleeps on his side instead, his shoulder makes the clearance between his neck and the bed surface increased, so the sleep pillow is preferably increased in height so as to provide sufficient support to his head and neck. However, all the existing sleep pillows are made with fixed height. While some pillows have curved profiles so as to provide different levels of height in one pillow, it is almost impossible that a human body can automatically align with the suitable area during sleep. In particular, prolonged sleeping on the side may have an adverse impact on blood circulation and in turn cause various physical problems, such as neck sprain, shoulder sprain or soreness, shoulder compression pain, compression paralysis, and even adhesive capsulitis. It is clear that sleep pillows unable to automatically adaptive their height to sleep posture leave the foregoing problems unmet and thus fail to address human physiological needs thereby enabling good sleep

SUMMARY OF THE INVENTION

In view of conventional sleep pillows that are made of fixed height and unable to adapt themselves to users' sleep posture, the present invention provides an air-bag-lifting sleep pillow structure, wherein the sleep pillow can sense its user's sleep posture and automatically modulate its height to appropriate level and can provide real-time modulation according to pre-stored personal settings, thereby helping to improve sleep quality, prevent sleeplessness, and mitigate sleep disorder. Particularly, the disclosed air-bag-lifting sleep pillow structure achieves height modulation using air bags, which are inflated by an air pump when it is desired to heighten the pillow, and are deflated when it is desired to lower the pillow height, thereby providing the most appropriate height for user's good sleep.

For achieving the foregoing objective, the air-bag-lifting sleep pillow structure of the present invention comprises a posture-sensing and commanding device installed on a user's body. The posture-sensing and commanding device detects the human body's sleep posture, and sends a signal about the human body's sleep posture to a sleep pillow in a wired or wireless manner. The sleep pillow then, according to the signal, automatically modulates the sleep pillow to the most appropriate height, so as to achieve the objective of the present invention. The human body posture-sensing and commanding device also supports height setting and remote turning on/off. The sleep pillow further comprises a signal-receiving and inflating-deflating control unit. The sleep pillow may also be provided with operational and control devices such as a switch, a charging port, an indication lamp, a power connecter, according to practical needs.

The disclosed sleep pillow for modulating height is composed of a base, an upper seat, a cushion support, and a cushion, wherein a variable-range space exists between the base and the upper seat for accommodating a height control unit and enabling height modulation.

The height control unit comprises an air pump, a muffling member, a vent valve, a check valve, a lifting device, a signal-receiving and inflating-deflating control unit, a battery, and a power connection device. The air pump enables inflation, and is connected to the muffling member through a pipe. The muffling member serves to reduce the noise generated when the air pump operates. The muffling member is connected to the check valve through a pipe. The check valve allows only one-way flow and maintains pressure. The check valve is further connected to the vent valve. The vent valve enables deflation. The vent valve is communicated with each of the lifting devices. The lifting device comprises an air bag. The air bag is of a substantially vertical bellows-like structure. The air bag is communicated with the air pump through the foregoing pipe device. The air bag is sandwiched between a base and an upper seat. A lower sleeve 444 is mounted around the air bag. The lower sleeve has its top provided with an upper outer retaining ring. The lower sleeve is assembled to a first sleeve, a second sleeve, and an upper sleeve in sequence. The first sleeve is internally provided with a first lower inner retaining ring at its bottom, a first lower outer retaining ring, and a first upper outer retaining ring at its top. The second sleeve has its bottom provided with a second lower inner retaining ring, and has its top provided with a second upper outer retaining ring. The upper sleeve has its bottom provided with a lower inner retaining ring. The upper outer retaining ring and the first lower inner retaining ring retain each other. The first upper outer retaining ring and the second lower inner retaining ring retain each other. The second upper outer retaining ring and the lower inner retaining ring retain each other. Thereby, the lower sleeve, the first sleeve, the second sleeve, and the upper sleeve are telescoped and can be extended and retracted without leaving each other.

The height control unit further has a signal-receiving and inflating-deflating control unit, a battery, and a height sensor. Therein, the signal-receiving and inflating-deflating control unit determines the height, and the battery powers the overall operation, while the height sensor senses the lifting or lowering movement of the sleep pillow.

The air bag may contain therein a spring member that helps to improve the lifting operation in terms of smoothness and powerfulness. The air bags may be arranged at four aspects of the pillow to keep the pillow surface level. The spring member is held in position at each of its top and bottom by a positioning member.

In the lifting device, a raised positioning structure may be formed on the first sleeve. The positioning structure comprises a ball. Another positioning structure is provided on the second sleeve encircling the first sleeve, which is a low-friction area positionally corresponding to the ball. The low-friction area is made of Teflon, having low friction coefficient that facilitates relative slide between the sleeves. With such a configuration, smooth sliding of the components is ensured.

DETAILED DESCRIPTION OF THE INVENTION

Figure 1:
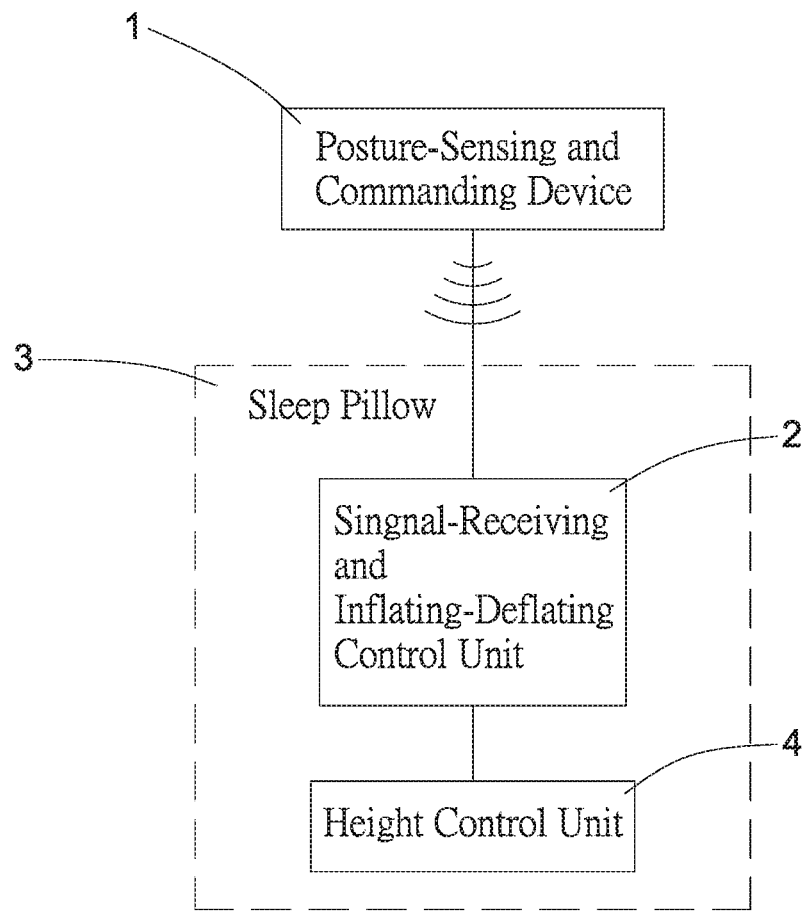
FIG. 1 is a structural block diagram of the present invention.

Referring to FIG. 1, according to the present invention, an air-bag-lifting sleep pillow structure comprises a posture-sensing and commanding device 1 installed on a human body. The posture-sensing and commanding device 1 detects the human body's sleep posture, and sends a signal about the human body's sleep posture to a sleep pillow 3 in a wired or wireless manner. The sleep pillow 3 then, according to the signal, automatically modulates the sleep pillow to the most appropriate height, so as to achieve the objective of the present invention. The sleep pillow 3 further comprises a signal-receiving and inflating-deflating control unit 2 and a height control unit 4. The sleep pillow 3 may also be provided with operational and control devices such as a switch, a charging port, an indication lamp, a power connecter, according to practical needs.

Figure 2:
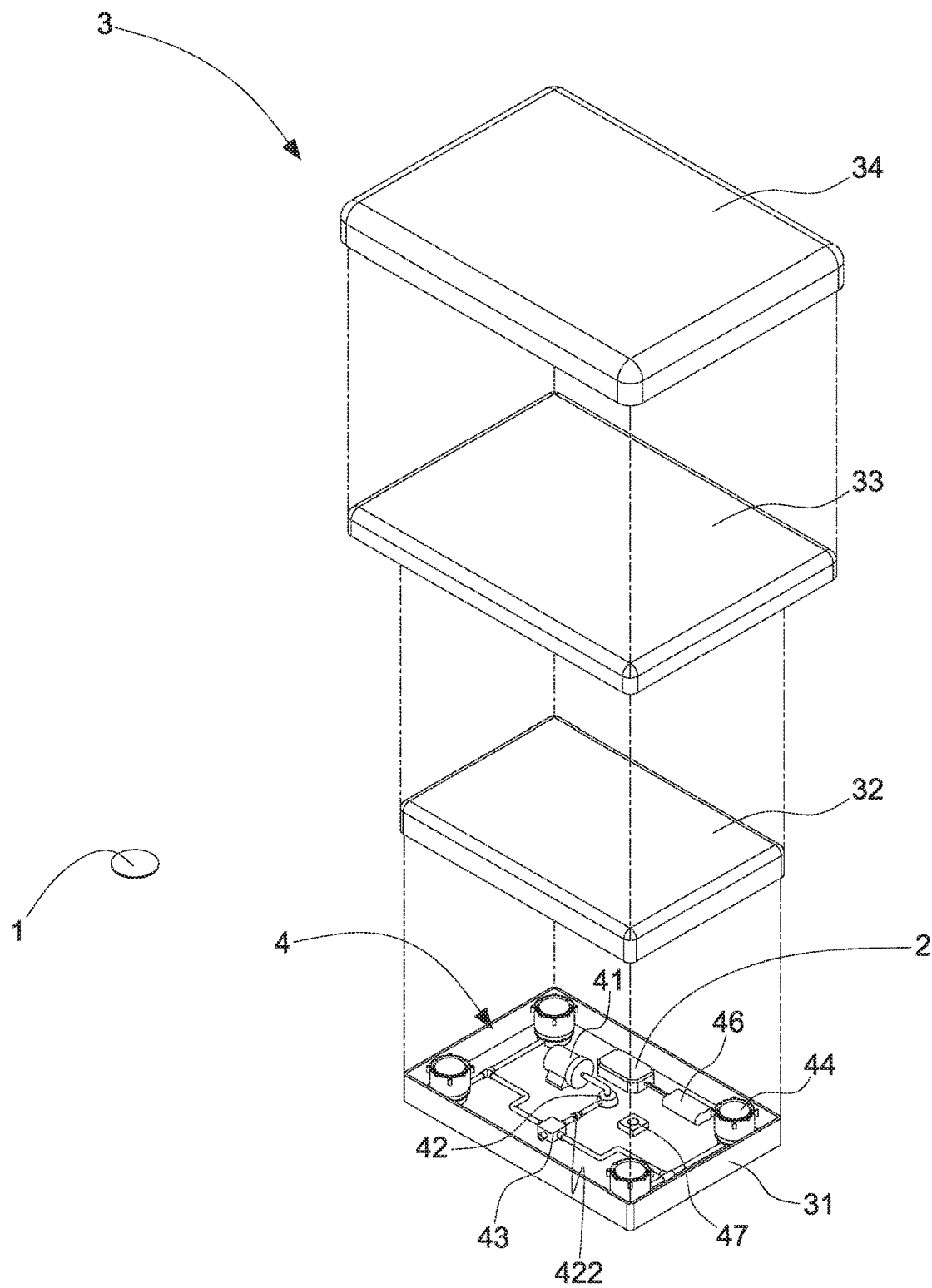
FIG. 2 is an exploded view of an air-bag-lifting sleep pillow structure of the present invention.
Figure 3:
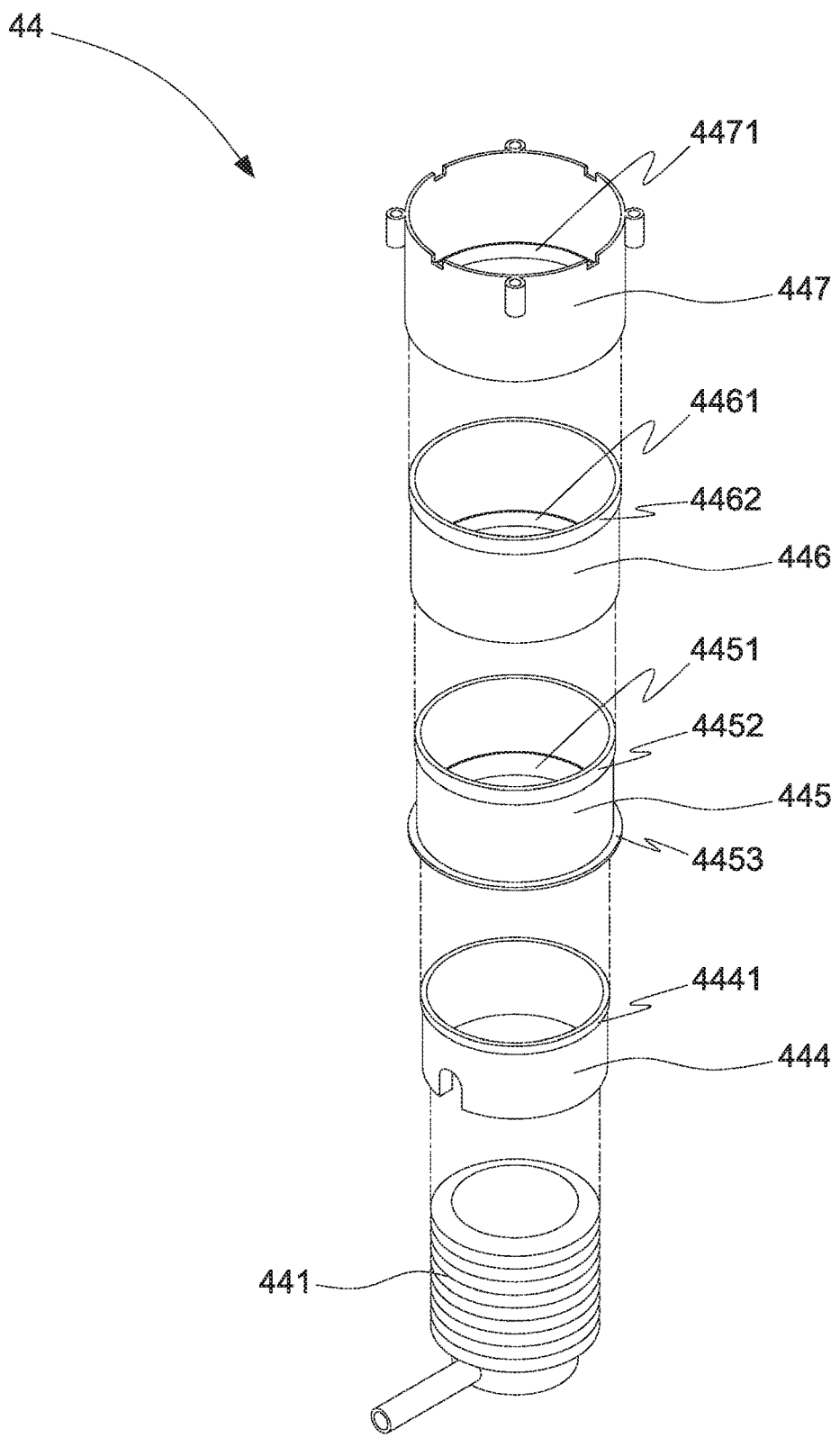
FIG. 3 is an exploded view of a lifting device of the air-bag-lifting sleep pillow structure.
Figure 4:
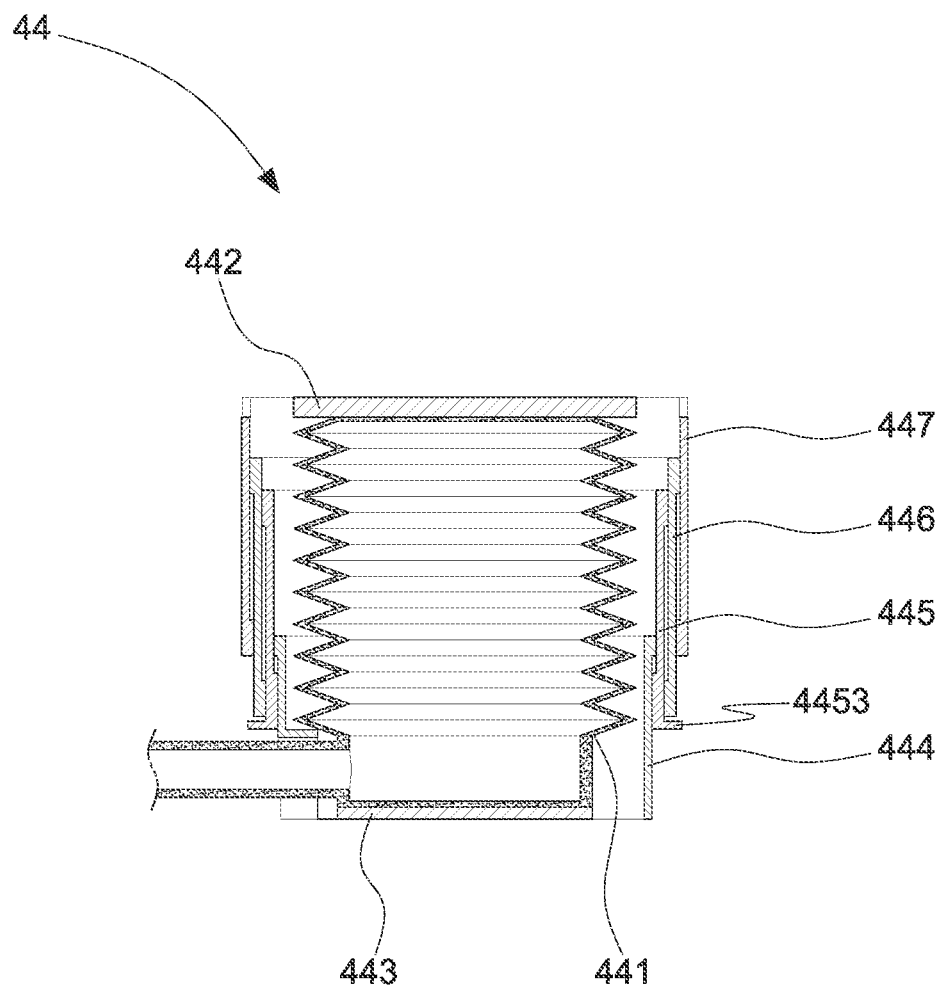
FIG. 4 is a cross-sectional view of the lifting device.

Also referring to FIG. 2, FIG. 3 and FIG. 4, the sleep pillow 3 has its form composed of a base 31, an upper seat 32, a cushion support 33, and a cushion 34. The base 31 and the upper seat 32 is separated by a space. The space is configured to accommodate a height control unit 4. The height control unit 4 comprises an air pump 41, a muffling member 42, a vent valve 43, a check valve 422, lifting devices 44, the signal-receiving and inflating-deflating control unit 2 and a battery 46. The air pump 41 provides inflation, and is connected to the muffling member 42 through a pipe. The muffling member 42 serves to reduce the noise generated when the air pump operates. The muffling member 42 is connected to the check valve 422 through a pipe. The check valve 422 allows only one-way flow and maintains pressure. The check valve 422 is further connected to the vent valve 43. The vent valve 43 enables deflation. The vent valve 43 is communicated with each of the lifting devices 44. The lifting device 44 comprises an air bag 441. The air bag 441 is of a substantially vertical bellows-like structure. The air bag 441 is communicated with the air pump 41. The air bag 441 is sandwiched between a bottom plate 443 and an upper seat 442. A lower sleeve 444 is mounted around the air bag 441. The lower sleeve 444 has its top provided with an upper outer retaining ring 4441. The lower sleeve 444 is assembled to a first sleeve 445, a second sleeve 446, and an upper sleeve 447 in sequence. The first sleeve 445 is internally provided with a first lower inner retaining ring 4451 at its bottom, a first lower outer retaining ring 4453, and a first upper outer retaining ring 4452 at its top. The second sleeve 446 has its bottom provided with a second lower inner retaining ring 4461, and has its top provided with a second upper outer retaining ring 4462. The upper sleeve 447 has its bottom provided with a lower inner retaining ring 4471. The upper outer retaining ring 4441 and the first lower inner retaining ring 4451 retain each other. The first upper outer retaining ring 4452 and the second lower inner retaining ring 4461 retain each other. The second upper outer retaining ring 4462 and the lower inner retaining ring 4471 retain each other. Thereby, the lower sleeve 444, the first sleeve 445, the second sleeve 446, and the upper sleeve 447 are telescoped and can be extended and retracted without leaving each other.

The height control unit 4 further has a signal-receiving and inflating-deflating control unit 2, a battery 46, and a height sensor 47. Therein, the signal-receiving and inflating-deflating control unit 2 determines the height, and the battery 46 powers the overall operation, while the height sensor 47 senses the lifting or lowering movement of the sleep pillow 3.

Figure 5:
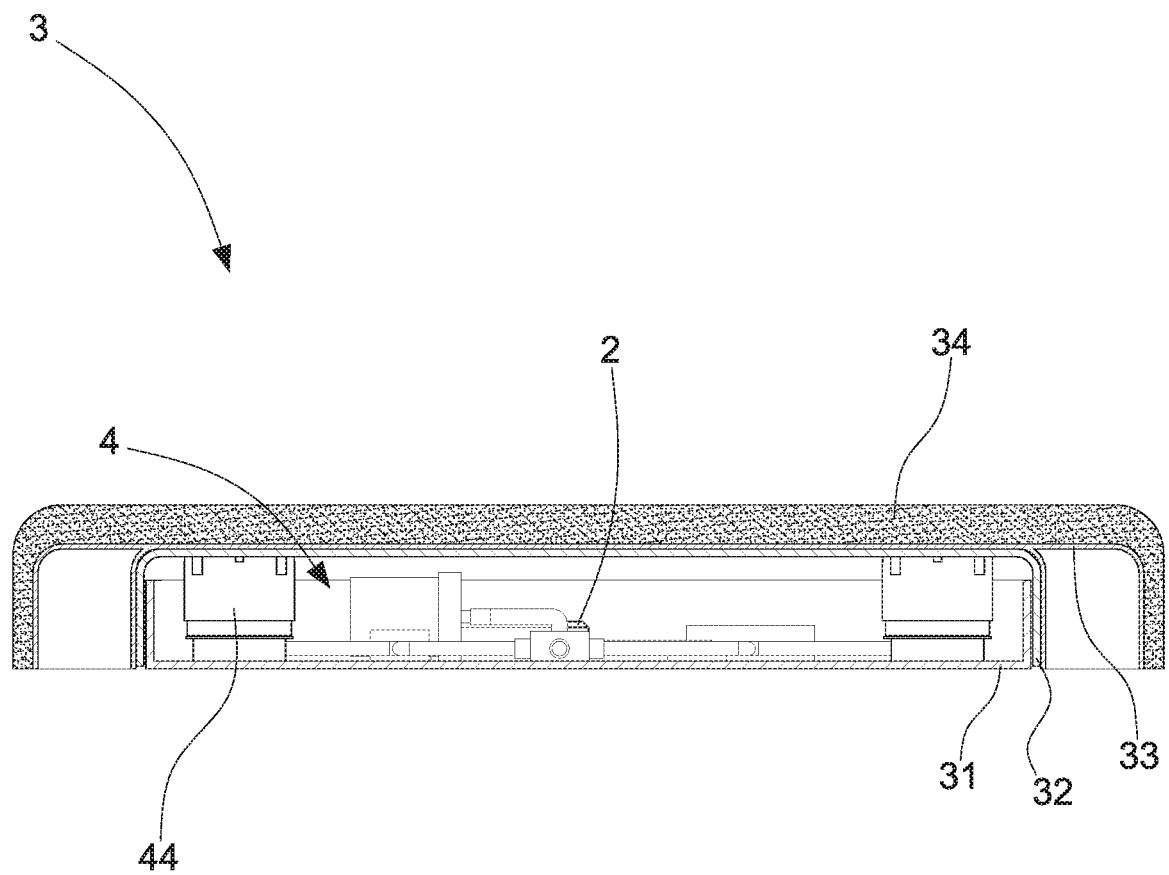
FIG. 5 is a cross-sectional view of the sleep pillow structure not raised.
Figure 6:
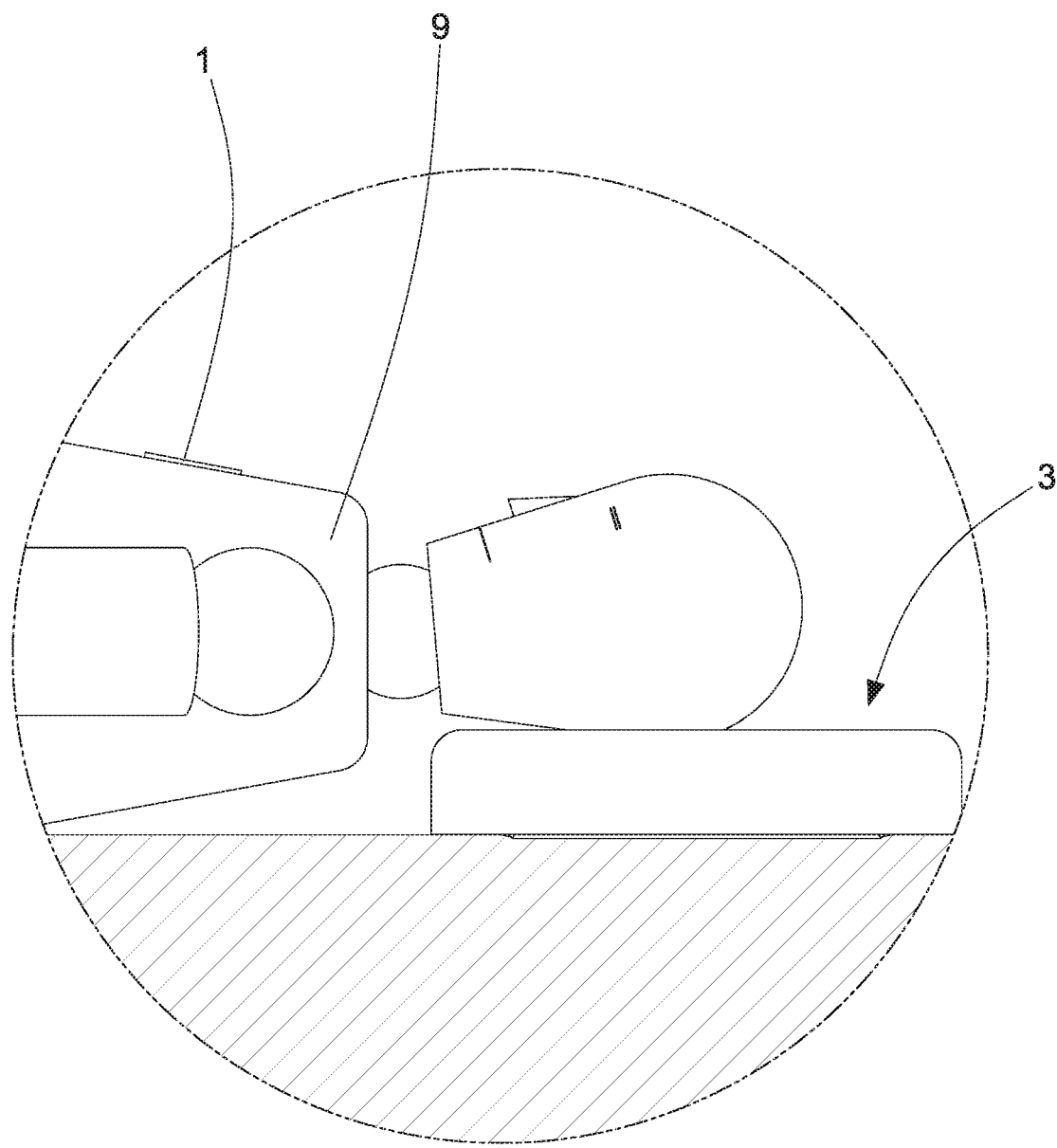
FIG. 6 is an applied of the sleep pillow structure on which a user is sleeping on his back.

In use of the present invention, as shown in FIG. 5 and FIG. 6, when a user 9 is sleeping on his back, the posture-sensing and commanding device 1 learns his sleep posture, and makes the sleep pillow 3 relatively low.

Figure 7:
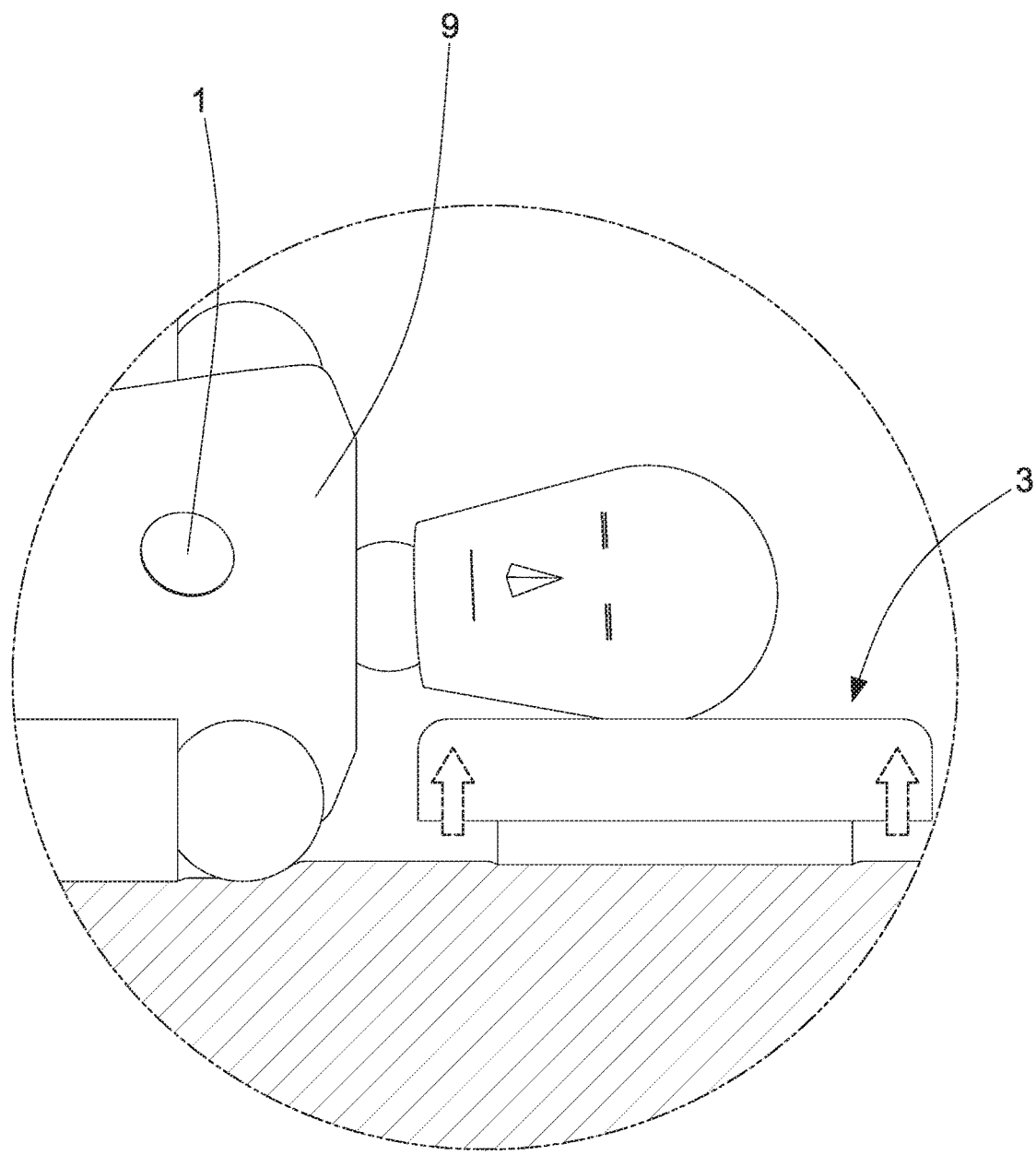
FIG. 7 is an applied of the sleep pillow structure on which a user is sleeping on his side.
Figure 8:
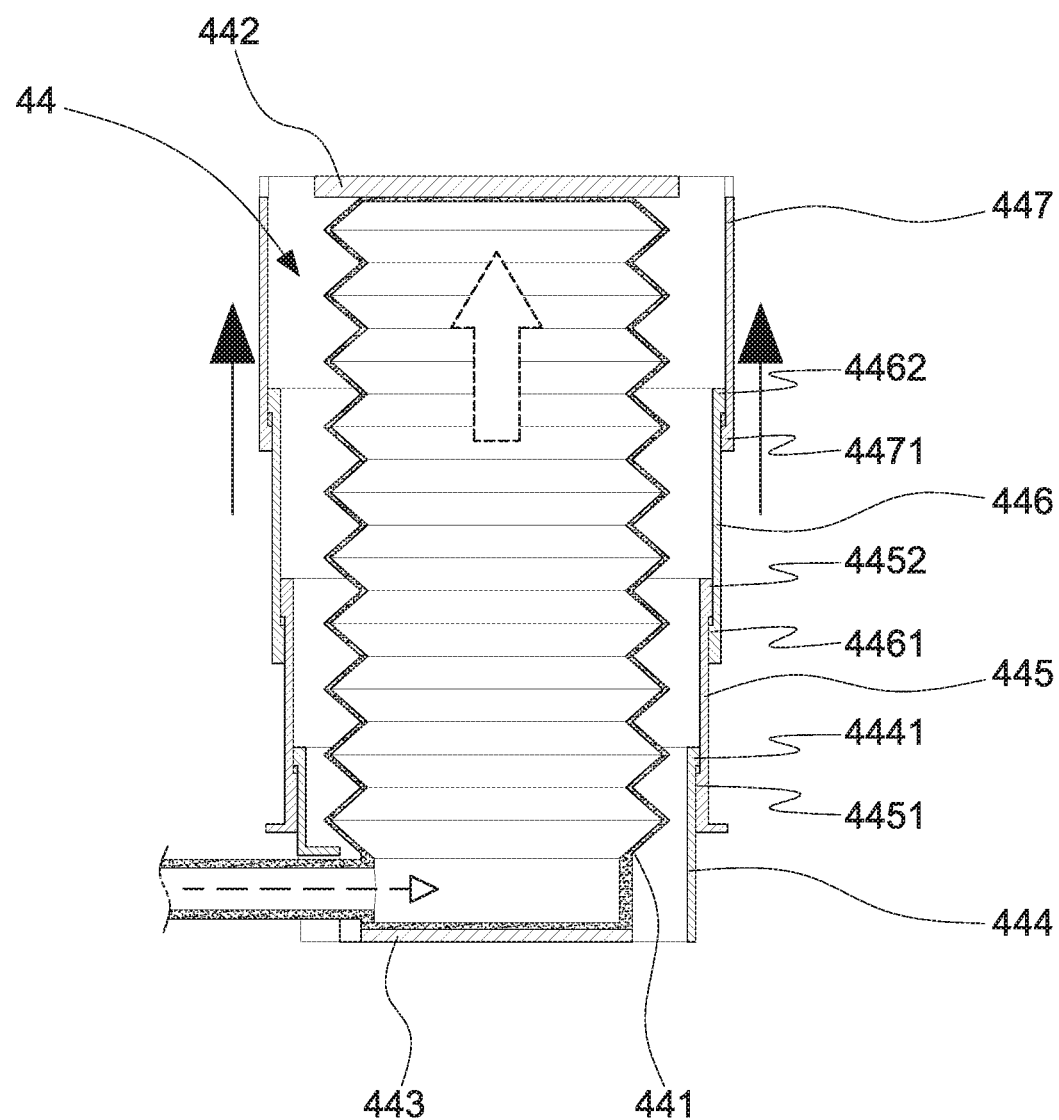
FIG. 8 is a schematic drawing showing the lifting device inflated and extended.
Figure 9:
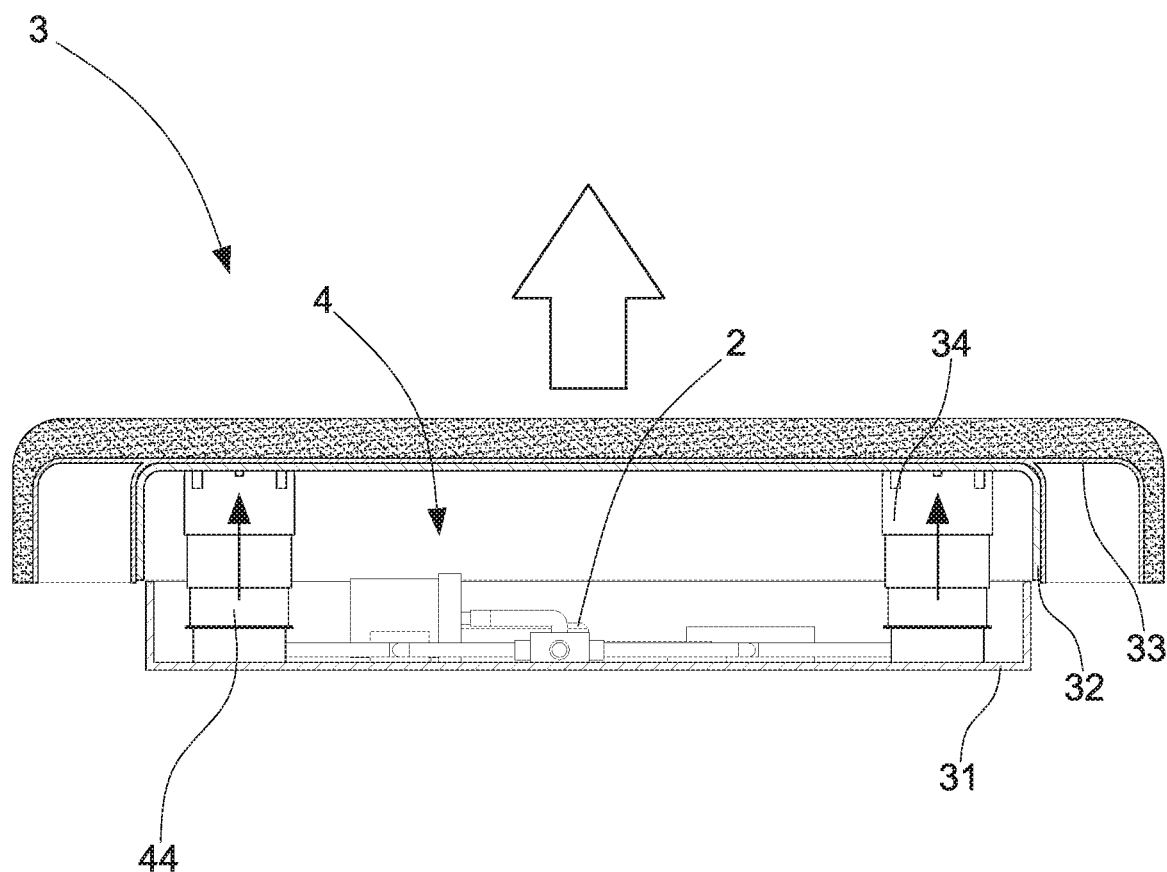
FIG. 9 is a schematic drawing showing the sleep pillow structure raised.

As shown in FIG. 7, FIG. 8 and FIG. 9, when the user 9 is now sleeping on his side instead, the posture-sensing and commanding device 1 learns his sleep posture, and determines that the sleep pillow 3 has to be raised. Consequently, it directs the air pump 41 to inflate the air bags 441, so that the top surface of the sleep pillow 3 is lifted, thereby providing the user with the most appropriate height that supports his head best.

Figure 10:
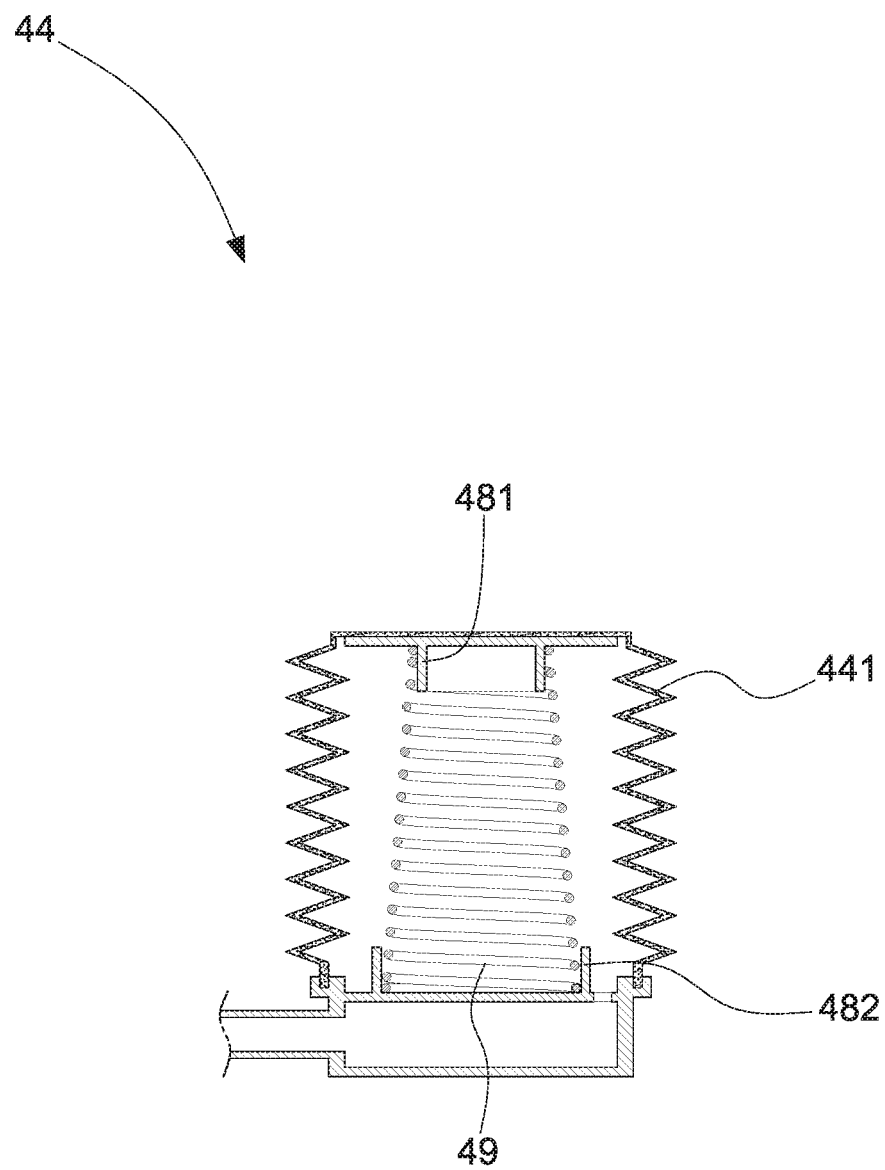
FIG. 10 depicts another embodiment of the present invention wherein a spring member is provided in the lifting device's air bag.
Figure 11:
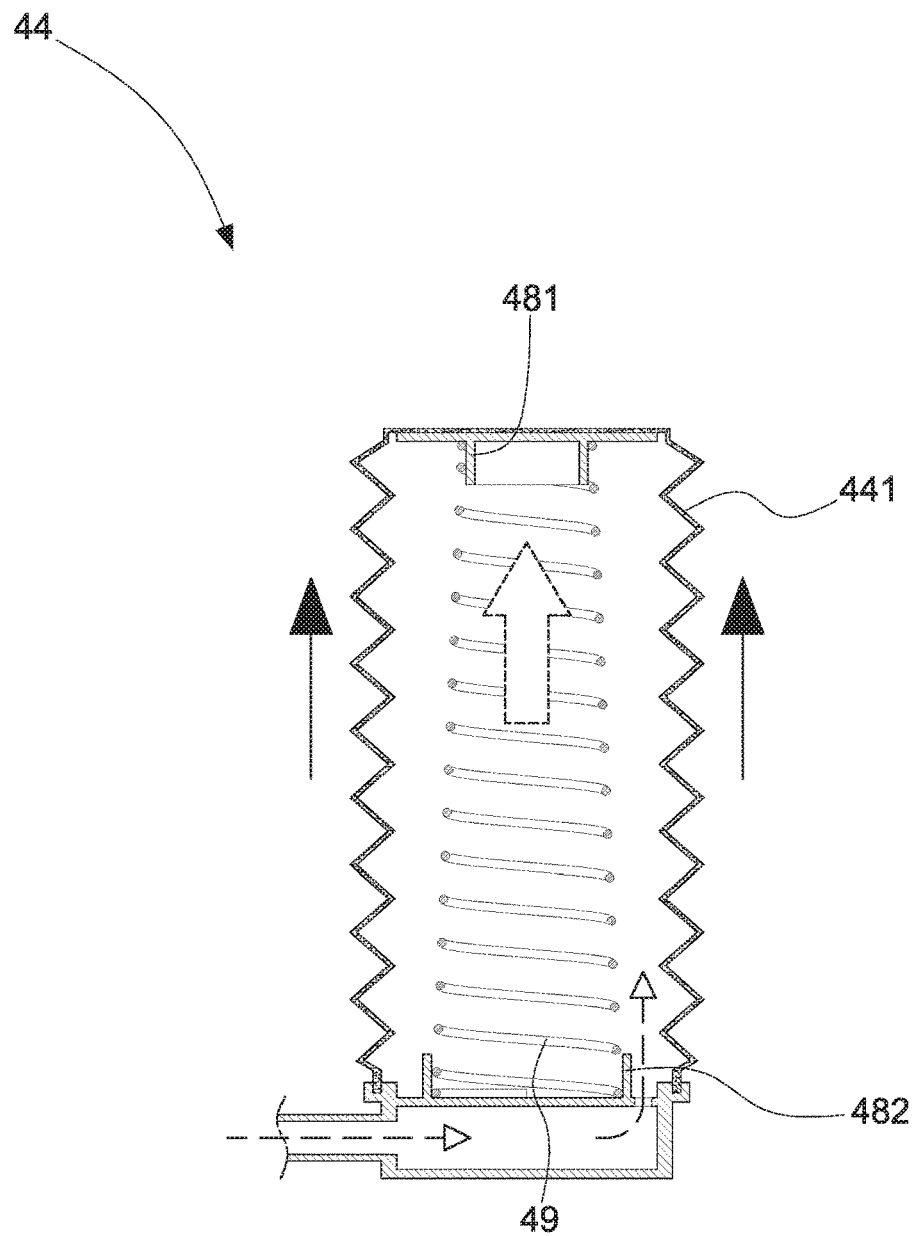
FIG. 11 is a schematic drawing showing operation of the lifting device of FIG. 10.

When the user 9 changes back to sleeping on his back again and the sleep pillow 3 needs to be lowered, the vent valve 43 is opened so as to release some air form the air bags 441, thereby automatically lowering the sleep pillow 3 in height. Referring to FIG. 10 and FIG. 11, in another embodiment of the present invention, the air bag 441 contains therein a spring member 49. The spring member 49 in the air bag 441 helps to improve the lifting operation in terms of smoothness and powerfulness. The spring member 49 is held in position by positioning members 481, 482.

Figure 12:
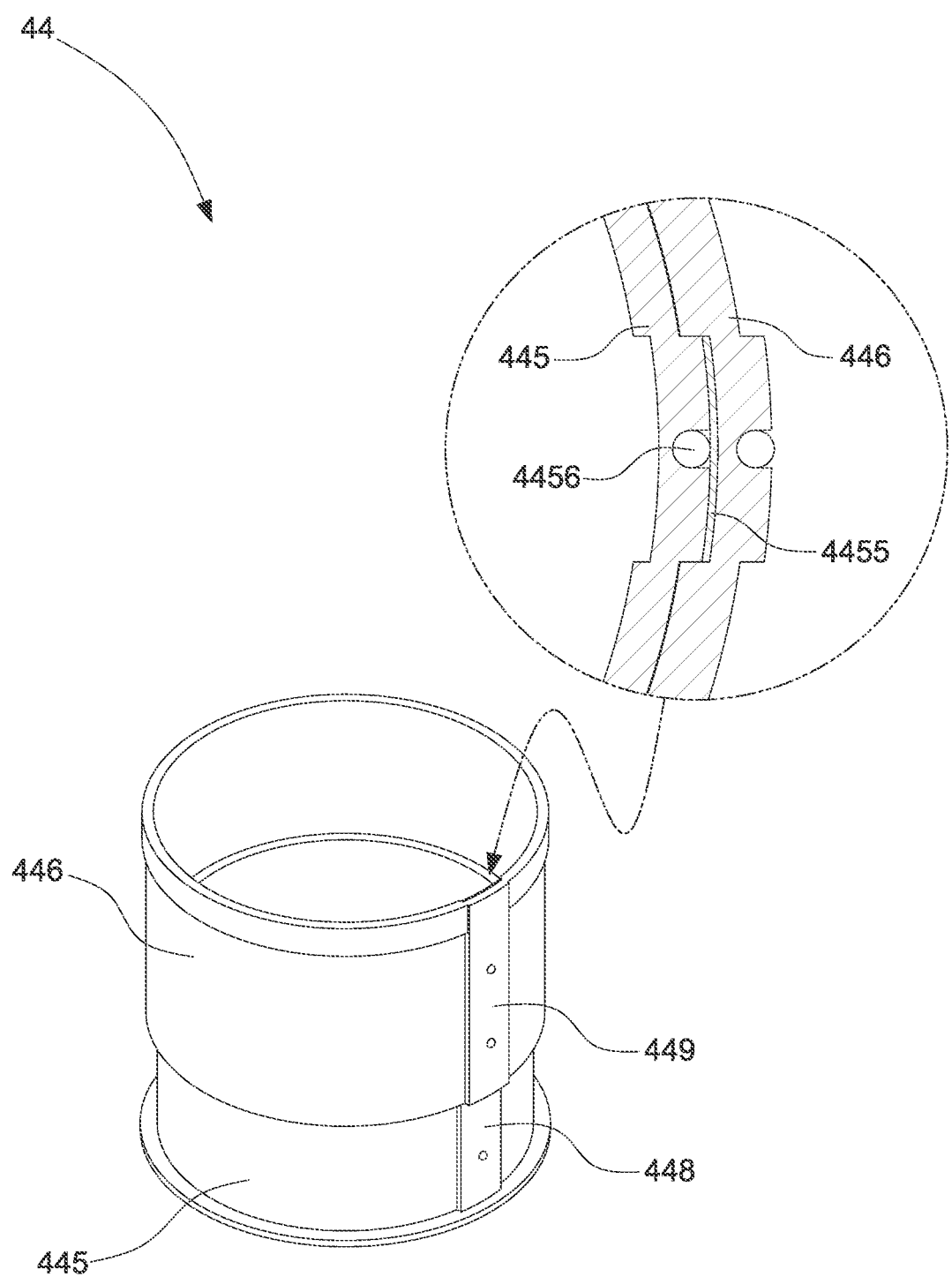
FIG. 12 depicts still another embodiment of the lifting device of the present invention.

Referring to FIG. 12, in the lifting device 44, a first raised positioning structure 448 may be formed on the first sleeve 445. The first raised positioning structure 448 comprises a ball 4456. A second raised positioning structure 449 is provided on the second sleeve 446 encircling the first sleeve 445. A low-friction area 4455 is disposed between the first raised positioning structure 448 and the second raised positioning structure 449 and corresponds to the ball 4456. The low-friction area 4455 is made of Teflon, having a low friction coefficient that facilitates relative sliding between the sleeves 445, 446. With such a configuration, smooth sliding of the components is ensured.

What is claimed is:

1. An air-bag-lifting sleep pillow structure, comprising:
   a posture-sensing and commanding device, which is configured to perform detection on a sleep posture of a user sleeping with the structure, and generate an electronic signal according to a result of the detection; and
   a sleep pillow, which contains therein a height control unit for receiving the electronic signal from the posture-sensing and commanding device and modulating the sleep pillow in height,
   wherein the height control unit comprises one or more lifting devices, each of the lifting devices comprises an air bag;
   wherein the air bag is sandwiched between a base and an upper seat, and a bottom of the air bag is sleeved by a third sleeve; a third upper outer retaining ring is disposed atop the third sleeve; the third sleeve being assembled to a first sleeve, a second sleeve, and an upper sleeve in sequence; a bottom of the first sleeve provided with a first lower inner retaining ring and a first lower outer retaining ring, and a top of the first sleeve provided with a first upper outer retaining ring; a bottom of the second sleeve provided with a second lower inner retaining ring, and a top of the second sleeve provided with a second upper outer retaining ring; a bottom of the upper sleeve provided with a third lower inner retaining ring; the third upper outer retaining ring and the first lower inner retaining ring retaining each other, the first upper outer retaining ring and the second lower inner retaining ring retaining each other, and the second upper outer retaining ring and the third lower inner retaining ring retaining each other;
   wherein the first sleeve of the lifting device is provided with a first raised positioning structure comprising a ball, and the second sleeve is provided with a second raised positioning structure having a low-friction area made of polytetrafluoroethylene(PTFE) disposed corresponding to the ball; and
   wherein the ball is fully accommodated inside a cavity of the first raised positioning structure.

2. The air-bag-lifting sleep pillow structure of claim 1, wherein the sleep pillow further comprises a signal-receiving and inflating-deflating control unit, and the sleep pillow has a control box connected to the signal-receiving and inflating-deflating control unit.

3. The air-bag-lifting sleep pillow structure of claim 1, wherein the sleep pillow is structurally composed of a base, an upper seat, a cushion support, and a cushion, in which the base and the upper seat is separated by a space, the space is configured to accommodate the height control unit.

4. The air-bag-lifting sleep pillow structure of claim 1, wherein the height control unit comprises an air pump, which is connected to a muffling member, the muffling member is connected to a check valve, the check valve is connected to a vent valve, the vent valve is communicated with one or more of the lifting devices.

5. The air-bag-lifting sleep pillow structure of claim 4, wherein the air bag is substantially a vertical bellows-like structure and is communicated with the air pump.

6. The air-bag-lifting sleep pillow structure of claim 4, wherein the height control unit further has a signal-receiving and inflating-deflating control unit, a battery, and a height sensor.

7. The air-bag-lifting sleep pillow structure of claim 5, wherein the air bag contains therein a spring member, and the top and bottom of the spring member is held in position at each of its top and bottom by a positioning member.

\* \* \* \* \*